US012746135B2

(12) United States Patent
Slazas

(10) Patent No.: US 12,746,135 B2
(45) Date of Patent: Sep. 29, 2026

(54) IMPLANTABLE STENT HAVING STRUCTURAL EXTENSION MEMBERS WITH GROWTH PROMOTING STRUCTURAL ELEMENTS FOSTERING GROWTH OF SURROUNDING TISSUE THERETO

(71) Applicant: DePuy Synthes Products, Inc., Raynham, MA (US)

(72) Inventor: Robert Slazas, Pinecrest, FL (US)

(73) Assignee: DePuy Synthes Products, Inc., Raynham, MA (US)

( * ) Notice: Subject to any disclaimer, the term of this patent is extended or adjusted under 35 U.S.C. 154(b) by 833 days.

(21) Appl. No.: 18/158,811

(22) Filed: Jan. 24, 2023

(65) Prior Publication Data

US 2024/0245536 A1    Jul. 25, 2024

(51) Int. Cl.

*A61F 2/848* (2013.01)
*A61F 2/00* (2006.01)
*A61F 2/82* (2013.01)

(52) U.S. Cl.

CPC ...... *A61F 2/848* (2013.01); *A61F 2002/0081* (2013.01); *A61F 2002/823* (2013.01); *A61F 2240/001* (2013.01); *A61F 2250/0026* (2013.01)

(58) Field of Classification Search

CPC .............. A61F 2/848; A61F 2002/0081; A61F 2002/823; A61F 2240/001;

(Continued)

(56) References Cited

U.S. PATENT DOCUMENTS 5,681,345 A * 10/1997 Euteneuer ............. A61L 31/044 606/198
5,993,482 A * 11/1999 Chuter ...................... A61F 2/90 623/1.15

(Continued)

FOREIGN PATENT DOCUMENTS

EP 2175901 3/2012
EP 1455687 9/2014

OTHER PUBLICATIONS

International Search Report and Written Opinion issued in International Application No. PCT/IB2024/050409, dated Apr. 4, 2024.

*Primary Examiner* — Sarah W Aleman
*Assistant Examiner* — Rachel S Highland
(74) *Attorney, Agent, or Firm* — Troutman Pepper Locke LLP

(57) ABSTRACT

An implantable stent forming a tubular scaffolding including a plurality of individual struts arranged in a pattern defining open spaces. The tubular scaffolding with a lumen defined therethrough having a lumen facing surface facing radially inward toward the lumen and an opposite tissue facing surface facing radially outward away from the lumen. Each individual strut has a longitudinal axis and a lateral cross-section with opposing sides extending between the lumen facing surface and the tissue facing surface. Furthermore, at least one structural extension member associated with one of the individual struts, wherein the structural extension member extends in a direction perpendicular to the longitudinal axis outward from one of the opposing sides of the associated individual strut and the structural extension member has a plurality of growth promoting structural elements.

19 Claims, 3 Drawing Sheets

(58) Field of Classification Search
CPC ...... A61F 2250/0026; A61F 2/91; A61F 2/90; A61F 2/0077; A61F 2230/0017; A61F 2230/0034; A61F 2250/0039; A61F 2250/0051
See application file for complete search history.

(56) References Cited

U.S. PATENT DOCUMENTS 6,231,581 B1 * 5/2001 Shank .................. A61B 17/064 606/157
6,494,906 B1 * 12/2002 Owens ...................... A61F 2/91 623/1.11
8,715,334 B2 5/2014 Clerc et al.
8,834,553 B2 * 9/2014 Melanson ................. A61F 2/04 606/232
9,265,596 B2 2/2016 Shank et al.
9,278,018 B2 3/2016 Roeder
9,517,122 B2 12/2016 Firstenberg et al.
9,526,640 B2 12/2016 Bertolino et al.
9,532,792 B2 1/2017 Galdonik et al.
9,532,873 B2 1/2017 Kelley
9,533,344 B2 1/2017 Monetti et al.
9,539,011 B2 1/2017 Chen et al.
9,539,022 B2 1/2017 Bowman
9,539,122 B2 1/2017 Burke et al.
9,539,382 B2 1/2017 Nelson
9,549,830 B2 1/2017 Bruszewski et al.
9,554,805 B2 1/2017 Tompkins et al.
9,561,125 B2 2/2017 Bowman et al.
9,572,982 B2 2/2017 Burnes et al.
9,579,484 B2 2/2017 Barnell
9,585,642 B2 3/2017 Dinsmoor et al.
9,615,832 B2 4/2017 Bose et al.
9,615,951 B2 4/2017 Bennett et al.
9,622,753 B2 4/2017 Cox
9,636,115 B2 5/2017 Henry et al.
9,636,439 B2 5/2017 Chu et al.
9,642,675 B2 5/2017 Werneth et al.
9,655,633 B2 5/2017 Leynov et al.
9,655,645 B2 5/2017 Staunton
9,655,989 B2 5/2017 Cruise et al.
9,662,129 B2 5/2017 Galdonik et al.
9,662,238 B2 5/2017 Dwork et al.
9,662,425 B2 5/2017 Lilja et al.
9,668,898 B2 6/2017 Wong
9,675,477 B2 6/2017 Thompson
9,675,782 B2 6/2017 Connolly
9,676,022 B2 6/2017 Ensign et al.
9,692,557 B2 6/2017 Murphy
9,693,852 B2 7/2017 Lam et al.
9,700,262 B2 7/2017 Janik et al.
9,700,399 B2 7/2017 Acosta-Acevedo
9,717,421 B2 8/2017 Griswold et al.
9,717,500 B2 8/2017 Tieu et al.
9,717,502 B2 8/2017 Teoh et al.
9,724,103 B2 8/2017 Cruise et al.
9,724,526 B2 8/2017 Strother et al.
9,750,565 B2 9/2017 Bloom et al.
9,757,260 B2 9/2017 Greenan
9,764,111 B2 9/2017 Gulachenski
9,770,251 B2 9/2017 Bowman et al.
9,770,577 B2 9/2017 Li et al.
9,775,621 B2 10/2017 Tompkins et al.
9,775,706 B2 10/2017 Peterson et al.
9,775,732 B2 10/2017 Khenansho
9,788,800 B2 10/2017 Mayoras, Jr.
9,795,391 B2 10/2017 Saatchi et al.
9,801,980 B2 10/2017 Karino et al.
9,808,599 B2 11/2017 Bowman et al.
9,833,252 B2 12/2017 Sepetka et al.
9,833,604 B2 12/2017 Lam et al.
9,833,625 B2 12/2017 Waldhauser et al.
10,219,921 B2 3/2019 Harris et al.
10,441,406 B2 10/2019 Firstenberg et al.
10,603,193 B2 3/2020 Folan et al.
11,033,411 B2 6/2021 Folan
11,382,776 B2 7/2022 Bluecher et al.
2001/0016770 A1 * 8/2001 Allen ...................... A61F 2/915 623/1.15
2002/0198593 A1 * 12/2002 Gomez ..................... A61F 2/91 623/1.16
2003/0144725 A1 * 7/2003 Lombardi ................. A61F 2/07 623/1.13
2004/0006382 A1 * 1/2004 Sohier ....................... A61F 2/91 623/1.42
2004/0093073 A1 * 5/2004 Lowe ........................ A61F 2/91 623/1.15
2004/0215324 A1 * 10/2004 Vonderwalde ............ A61F 2/91 623/1.15
2005/0102024 A1 * 5/2005 Riccotta .................... A61F 2/07 623/1.36
2007/0123973 A1 5/2007 Roth et al.
2009/0187240 A1 7/2009 Clerc et al.
2009/0248132 A1 10/2009 Bloom et al.
2013/0023982 A1 1/2013 Uchiyama et al.
2013/0172982 A1 * 7/2013 Pacetti ...................... A61F 2/91 623/1.15
2014/0114435 A1 4/2014 Carpenter et al.
2014/0277562 A1 9/2014 Seddon et al.
2017/0007264 A1 1/2017 Cruise et al.
2017/0007265 A1 1/2017 Guo et al.
2017/0020670 A1 1/2017 Murray et al.
2017/0020700 A1 1/2017 Bienvenu et al.
2017/0027640 A1 2/2017 Kunis et al.
2017/0027692 A1 2/2017 Bonhoeffer et al.
2017/0027725 A1 2/2017 Argentine
2017/0035436 A1 2/2017 Morita
2017/0035567 A1 2/2017 Duffy
2017/0042548 A1 2/2017 Lam
2017/0049596 A1 2/2017 Schabert
2017/0071737 A1 3/2017 Kelley
2017/0072452 A1 3/2017 Monetti et al.
2017/0079671 A1 3/2017 Morero et al.
2017/0079680 A1 3/2017 Bowman
2017/0079766 A1 3/2017 Wang et al.
2017/0079767 A1 3/2017 Leon-Yip
2017/0079812 A1 3/2017 Lam et al.
2017/0079817 A1 3/2017 Sepetka et al.
2017/0079819 A1 3/2017 Pung et al.
2017/0079820 A1 3/2017 Lam et al.
2017/0086851 A1 3/2017 Wallace et al.
2017/0086996 A1 3/2017 Peterson et al.
2017/0095259 A1 4/2017 Tompkins et al.
2017/0100126 A1 4/2017 Bowman et al.
2017/0100141 A1 4/2017 Morero et al.
2017/0100143 A1 4/2017 Grandfield
2017/0100183 A1 4/2017 Iaizzo et al.
2017/0113023 A1 4/2017 Steingisser et al.
2017/0147765 A1 5/2017 Mehta
2017/0151032 A1 6/2017 Loisel
2017/0165062 A1 6/2017 Rothstein
2017/0165065 A1 6/2017 Rothstein et al.
2017/0165454 A1 6/2017 Tuohy et al.
2017/0172581 A1 6/2017 Bose et al.
2017/0172766 A1 6/2017 Vong et al.
2017/0172772 A1 6/2017 Khenansho
2017/0189033 A1 7/2017 Sepetka et al.
2017/0189035 A1 7/2017 Porter
2017/0215902 A1 8/2017 Leynov et al.
2017/0216484 A1 8/2017 Cruise et al.
2017/0224350 A1 8/2017 Shimizu et al.
2017/0224355 A1 8/2017 Bowman et al.
2017/0224467 A1 8/2017 Piccagli et al.
2017/0224511 A1 8/2017 Dwork et al.
2017/0224953 A1 8/2017 Tran et al.
2017/0231749 A1 8/2017 Perkins et al.
2017/0252064 A1 9/2017 Staunton
2017/0265983 A1 9/2017 Lam et al.
2017/0281192 A1 10/2017 Tieu et al.
2017/0281331 A1 10/2017 Perkins et al.
2017/0281344 A1 10/2017 Costello
2017/0281909 A1 10/2017 Northrop et al.
2017/0281912 A1 10/2017 Melder et al.

(56) References Cited

U.S. PATENT DOCUMENTS

| | | | |
|---|---|---|---|
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2019/0247207 A1 | 8/2019 | Sigmon, Jr. et al. |

* cited by examiner

IMPLANTABLE STENT HAVING STRUCTURAL EXTENSION MEMBERS WITH GROWTH PROMOTING STRUCTURAL ELEMENTS FOSTERING GROWTH OF SURROUNDING TISSUE THERETO

FIELD OF THE DISCLOSURE

The present disclosure relates to an implantable medical device remaining stable and stationary in position when implanted in a vessel at a target site. In particular, the disclosure is directed to an implantable neurovascular stent comprising a tubular scaffolding of a plurality of individual struts arranged in a pattern. Structural extension members associated with individual struts provide greater overall surface area while growth promoting structural elements associated therewith serve as targeted microsites fostering growth of the surrounding cellular tissue thereto. As a result, over time, as the surrounding cellular tissue grows in/on the growth promoting structural elements the extent and hence strength increases to which the implantable device is retained stationary in position at the target site within the vessel.

DESCRIPTION OF RELATED ART

In the current state of medical advancement, a significant number of medical devices are implantable in the human body. Implantable devices that are intended to remain implanted in the body have many requirements. Since implantable medical devices are in direct physical contact with bodily tissue and exposed to bodily fluids the design of these devices focuses on accomplishing their intended function while simultaneously being biocompatible (i.e., non-toxic), without eliciting a negative or defensive bodily reaction (e.g., irritation, inflammation, or all out rejection). Often the biocompatible material used to manufacture the implantable medical device is a shape memory alloy such as Nickel-Titanium (Nitinol)). In certain situations, to provide stability (i.e., prevent or minimize movement once implanted) it may be intended for the implantable medical device to incorporate into the surrounding tissue as quickly as possible. Under these circumstances, expediting or promoting incorporation or growth of surrounding bodily tissue thereto may be an additional factor when designing the implantable medical device.

An example implantable mechanical neurovascular treatment device intended to incorporate the surrounding tissue thereto as quickly as possible is a flow diverter comprising a self-expanding stent delivered intravascularly through the body to a target location in the brain using a plurality of ancillary devices (e.g., a guide catheter, a microcatheter, and a delivery wire) in the treatment of aneurysms. Once delivered via the microcatheter to the target site within the vessel, the expandable stent is unsheathed from the microcatheter. When unsheathed from the microcatheter the stent automatically transitions from a radially compressed state (i.e., non-deployed) to a radially expanded state (i.e., deployed) diverting blood flow away from the aneurysm. Alternatively, rather than automatically, the stent when unsheathed from the microcatheter may expand in response to a manual force (e.g., inflation of balloon disposed in the lumen of the stent).

Conventional stents are typically a cage or mesh scaffolding that is tubular in shape comprising a plurality of struts having a predetermined pattern defining spaces or openings therebetween. Within the tubular scaffolding a lumen is defined in an axial direction therethrough. Numerous factors may be selected in the design of the scaffolding, for example, the pattern of the struts, the porosity and/or thickness of the individual struts, etc. The tubular scaffolding may be manufactured by interweaving or braiding individual wires or filaments into the desired pattern with spaces or openings created therebetween. Alternatively, the manufacturing of the stent may begin with a cylindrical hypotube in which portions thereof are removed (e.g., cut out using a laser) creating spaces or openings therein whereby the remaining sections of the tube form a mesh or cage of individual struts interconnected in a predetermined desired pattern.

FIG. 1A depicts a conventional implantable self-expanding stent 10 comprising a plurality of struts 100 in a predetermined pattern with spaces or openings 103 defined therebetween. The stent 10 in FIG. 1A is a tubular scaffolding having a lumen defined axially therethrough from a proximal end 130 to an opposite distal end 135. Moreover, the tubular scaffolding has a lumen facing surface 110 (i.e., radially inward facing surface defining the lumen) and an opposite tissue facing surface 105 (i.e., radially outward facing surface relative to the lumen-when implanted in the vessel, the outward facing surface faces the surrounding bodily tissue). FIG. 1B is an enlarged view of section I(B) of the stent 10 in FIG. 1A. While FIG. 1C represents an enlarged perspective view of the lumen facing surface 110 of section I(C) illustrating an individual or single strut 100 of the tubular scaffolding in FIG. 1B.

In FIG. 1C a standard (x-y-z) three-dimensional coordinate legend is provided to aid in describing the thickness "T" and the width "W" of the individual strut 100. Specifically, the individual strut 100 is oriented with its center longitudinal axis (L-axis) parallel to the x-axis. FIG. 1D represents a radial cross-sectional view through the single strut 100 along line I(D)-I(D) of FIG. 1C, wherein the thickness "T" of the strut is measured along the z-axis, while the width "W" of the strut is measured along the y-axis. The exemplary individual strut in FIG. 1D has a four-sided radial cross-sectional shape in which the lumen facing surface 110 (radially inward surface of the tubular scaffolding) is curved, domed, or humped while the opposite tissue facing surface 105 is planar, linear, straight or flat. While each of the remaining two sides 115, 120 of the four-sided radial cross-sectional shape are: (i) planar, linear, straight or flat; (ii) parallel to one another; and (ii) perpendicular to the tissue facing surface 105.

While in a radially compressed state (i.e., non-deployed) the self-expanding stent is advanced via a delivery device (e.g., a microcatheter) through the vasculature to the target site. At which time the self-expanding stent, when unsheathed from the delivery device, is deployed automatically transitioning to a radially expanded state (returning to its original memory shape) in direct physical contact with the surrounding tissue (i.e., inner wall of the vasculature).

It is desirable to develop an improved implantable stent that remains stable and stationary in position when implanted in the vessel at the target site by promoting growth of the surrounding tissue thereto.

SUMMARY OF THE DISCLOSURE

An aspect of the disclosure is directed to an implantable stent that remains stable and fixed in position when implanted in the vessel at the target site by promoting growth of the surrounding tissue thereto.

Another aspect of the disclosure relates to an implantable stent comprising a plurality of individual struts arranged in a pattern. Structural extension members associated with individual struts provide greater overall surface area and growth promoting structural elements associated therewith serve as targeted microsites fostering growth of the surrounding cellular tissue thereto. As a result, over time, as the surrounding cellular tissue grows in/on the growth promoting structural elements the extent and hence strength increases to which the implantable device is retained stationary in position at the target site within the vessel.

BRIEF DESCRIPTION OF THE DRAWING

The foregoing and other features of the disclosure will be more readily apparent from the following detailed description and illustrative drawings wherein like reference numbers refer to similar elements throughout the several views and in which.

Figure 2A:
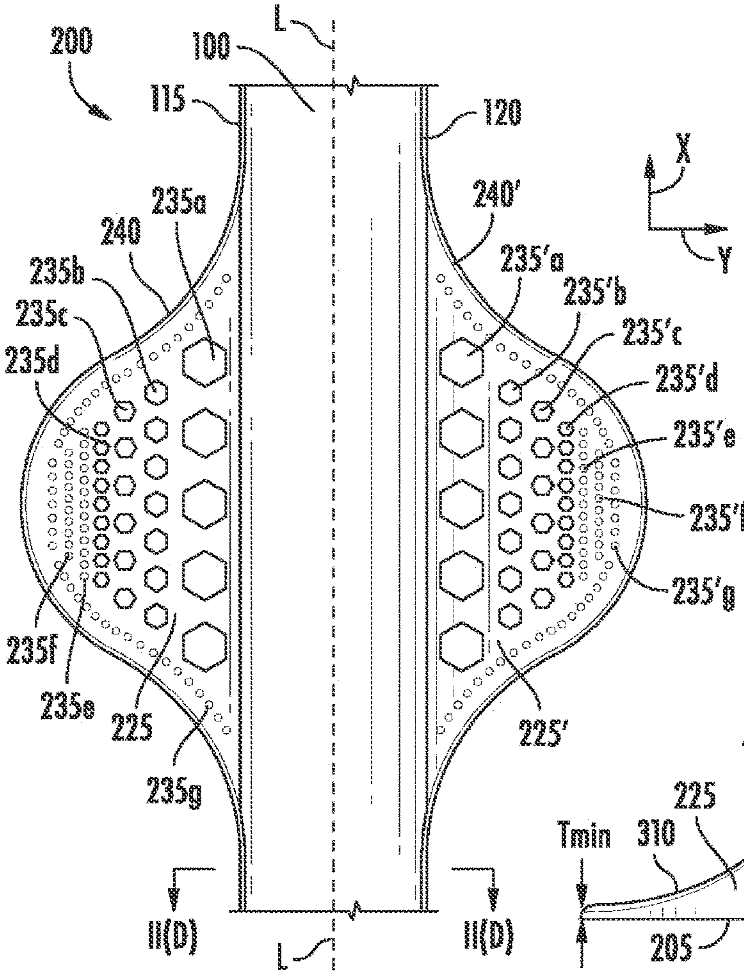
FIG. 2A is a lumen facing surface view of a section of an example tubular scaffolding of an implantable stent in accordance with the disclosure depicting an individual struct and associated structural extension members (e.g., flaps or wings) on respective sides thereof fully aligned with one another in a direction of the longitudinal L-axis through the individual strut.
Figure 2B:
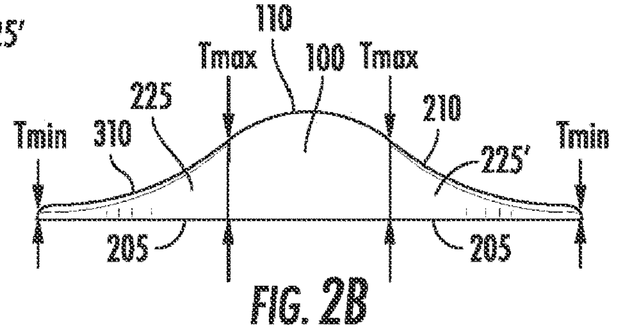
Figure 2C:
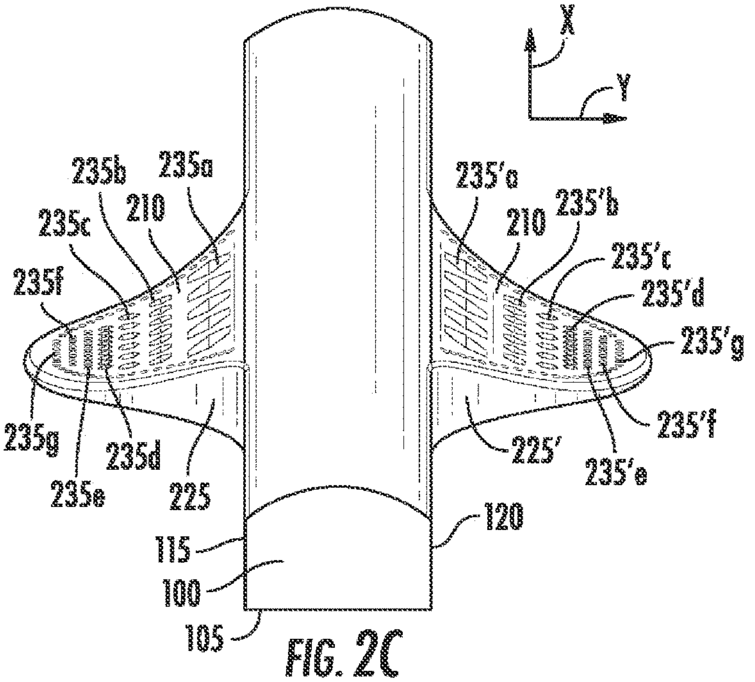
Figure 2D:
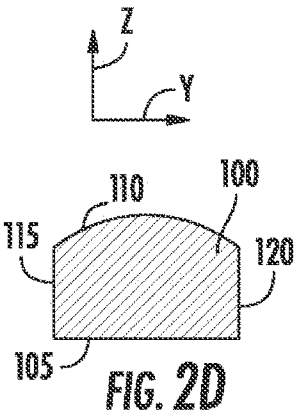
Figure 2E:
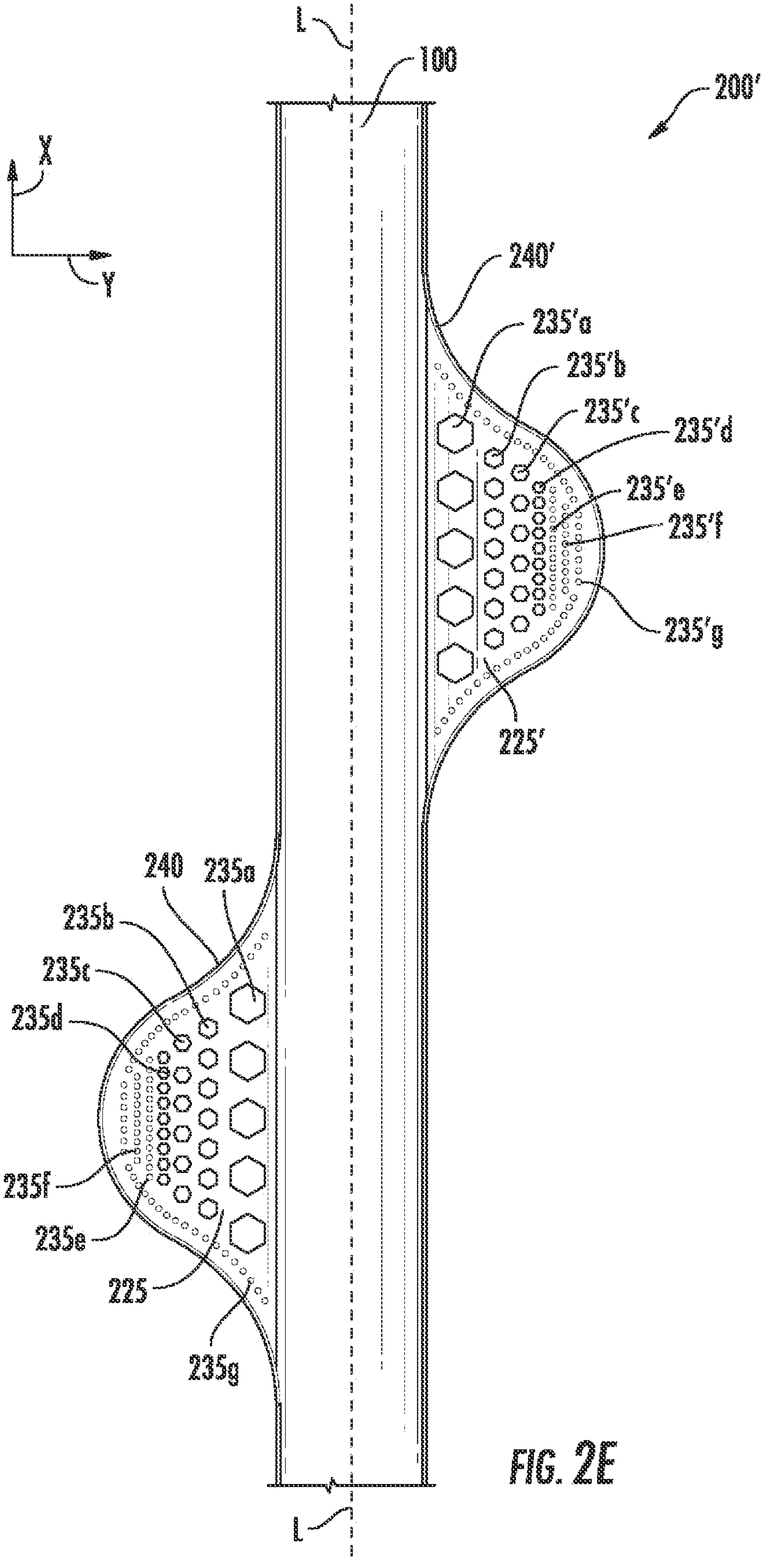

and wherein growth promoting structural elements associated with each structural extension member (e.g., flap or wing) serve as targeted microsites fostering growth of surrounding tissue thereto;

FIG. 2B is an end view (the view from either end is identical) of the section of the example tubular scaffolding in FIG. 2A;

FIG. 2C is a perspective view of the lumen facing surface of the section of the example tubular scaffolding in FIG. 2A;

FIG. 2D is a lateral cross-sectional view through the section of the example tubular scaffolding of FIG. 2A along lines II(D)-II(D); and FIG. 2E is a lumen facing surface view of a section of another example of the tubular scaffolding of the implantable stent in accordance with the disclosure depicting an individual struct and associated structural extension members (e.g., flaps or wings) on respective sides thereof fully offset (i.e., no overlap) from one another in the direction of the longitudinal L-axis through the individual strut; and wherein growth promoting structural elements associated with each structural extension member (e.g., flap or wing) serve as targeted microsites fostering growth of surrounding tissue thereto.

DETAILED DESCRIPTION OF THE DISCLOSURE

The terms "distal" or "proximal" are used in the following description with respect to a position or direction relative to the treating physician or medical interventionalist. "Distal" or "distally" are a position distant from or in a direction away from the physician or interventionalist and closest to or a direction towards the target site to be treated in the vessel. "Proximal" or "proximally" or "proximate" are a position near or in a direction toward the physician or medical interventionist and distance from or in a direction away from the target site to be treated in the vessel.

The present disclosure is directed to an implantable stent structurally designed to maintain stability and prevent movement by promoting growth of surrounding tissue thereto when implanted at the target site in a vessel. By way of non-limiting example, the implantable stent is a self-expanding tubular scaffolding comprising a plurality of interconnected struts having a desired pattern or configuration with free cell areas, spaces or openings defined therebetween. When designing the stent, the particular pattern of the struts forming the tubular scaffolding may be selected, as desired, based on the body anatomy (e.g., vasculature in the brain) and/or particular disorder to be treated (e.g., intracranial aneurysm). Since the modification in accordance with the disclosure is directed to the design or shape of individual struts comprising the tubular scaffolding of the implantable stent, the exemplary individual strut design is applicable for any desired pattern or arrangement of the struts. Moreover, the stent may be made of a biocompatible memory shape alloy (e.g., Nitinol) that self-expands when unsheathed from the microcatheter or otherwise may expand only when subject to an externally imposed manual force (e.g., radially outward expansion force from within the lumen such as by inflating a balloon disposed in the lumen of the stent). The application or use of the implantable stent is applicable to any anatomy (not limited to the brain) and any particular treatment (not limited to use as a flow diverter).

The tubular scaffolding of an implantable stent represents a plurality of individual struts interconnected in a desired pattern defining free areas, spaces or openings therebetween. In a lateral cross-section through the individual strut the "thickness" is the dimension between the lumen facing surface and the opposing tissue facing surface, while the "width" is the dimension between the opposing "sides," wherein each "side" extends from the lumen facing surface to the tissue facing surface. The opposing sides are typically parallel to one another and perpendicular to the tissue facing surface. In the case of a conventional implantable stent, each individual strut extending between two adjacent common vertex (e.g., overlap, intersection or interconnection of individual struts) has a uniform lateral cross-section (e.g., uniform in width in the y-direction) along a direction of the L-axis longitudinally through the individual strut.

An aspect of the disclosure is that along discrete regions of individual struts the width (i.e., in the y-direction, perpendicular to the L-axis longitudinally through the strut) of the tubular scaffolding is increased or extended beyond the respective sides of the individual strut thereby increasing the overall or cumulative surface area of the tubular scaffolding. In other words, along discrete regions at least some of the individual struts are configured to include structural extension members greater in width (in the y-direction) relative to those remaining regions of the individual struts in which the structural extension members are absent or not present. Any individual strut of the tubular scaffolding may have none, one or more than one associated structural extension member. The number of structural extension members (i.e., cumulative or overall surface area) and their arrangement along the individual struts forming the tubular scaffolding may be selected, as desired, based on such criteria as a desired amount of growth of surrounding tissue thereto to be produced, the longitudinal length of the individual strut between adjacent common vertex (e.g., overlap, intersection or interconnection of individual struts), and/or intended treatment with a specific anatomy.

Increased overall or cumulative surface area of individual struts is achieved in accordance with the example disclosure by altering its lateral cross-sectional shape, i.e., increasing the width (in the y-direction), along discrete sections. Specifically, the otherwise substantially uniform lateral cross-sectional shape is altered or modified along discrete sections thereof to include one or more structural extension members (e.g., flaps or wings) disposed on one or both (i.e., opposite) sides of the individual strut itself. The structural extension member is arranged at discrete regions along one or both (i.e., opposite) sides of the individual strut between adjacent common vertex. Accordingly, no portion of the structural extension member aligns, overlaps or coincides with any common vertex (e.g., overlap, intersection or interconnection of individual struts) of the tubular scaffolding.

The processing used to produce the implantable stent in accordance with the disclosure depends on whether the individual struts and associated structural extension members comprising the example tubular scaffolding are manufactured as an integral single unit or separate components secured together. Manufacturing of the example tubular scaffolding as an integral single unit may start with a single continuous piece of material formed into a tubular structure (e.g., hyoptube). Removal processing (e.g., laser cutting, mechanical cutting, stamping, perforating, and/or punching) is then used to remove areas/portions/sections of the hypotube forming both the individual struts as well as the structural extension members integral therewith. In contrast to removal of material, both the individual struts and associated structural extension members of the tubular scaffolding may be manufactured as an integral single unit by applying material (e.g., 3D printing). Alternatively, the structural extension members may be separate components from the individual struts of the tubular scaffolding. In such case, the tubular scaffolding may initially be formed by interweaving or braiding individual wires or filaments together formed into a tubular structure. Thereafter, the structural extension member(s) may be physically attached, mounted or secured directly to discrete regions along one or both sides of the interwoven/braided individual struts of the initially formed tubular scaffolding. When viewing a radial cross-section of an individual strut its "sides" are surfaces extending between the lumen facing surface and the tissue facing surface. Regardless of how the tubular scaffolding is manufactured, each structural extension member has associated therewith a plurality of growth promoting structural elements serving as targeted microsites that foster growth of the surrounding cellular tissue thereto when the stent is implanted in the body, as described in further detail below.

Figure 1A:
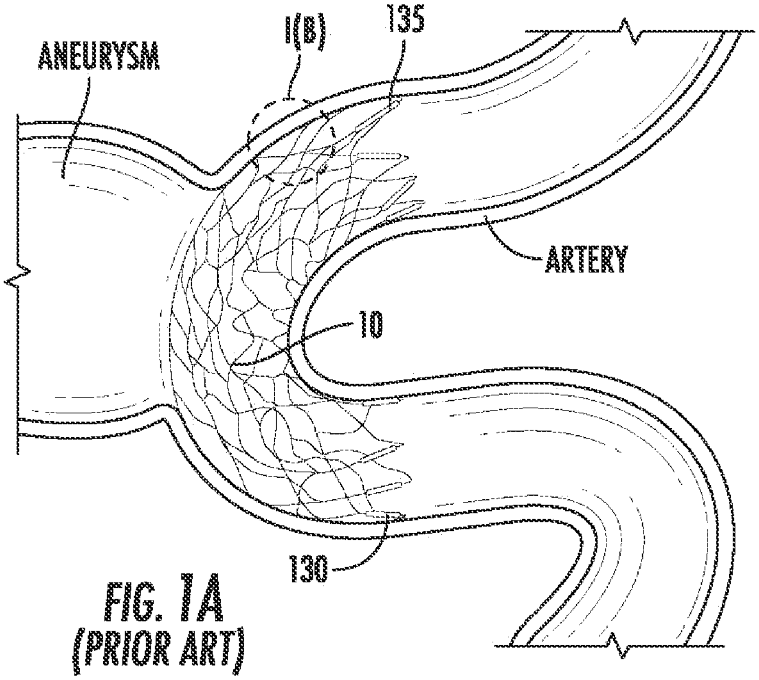
FIG. 1A (PRIOR ART)
FIG. 1A illustrates a schematic view of a Prior Art self-expanding stent flow diverter implanted in a vessel at a neck of an aneurysm to be treated; wherein the stent is depicted in a deployed (i.e., radially expanded) state.
Figure 1B:
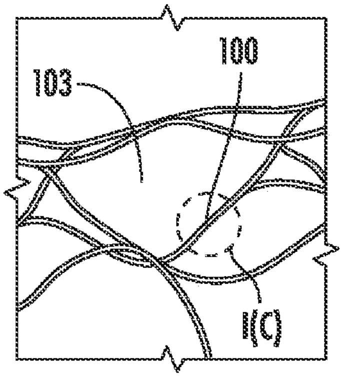
FIG. 1B (PRIOR ART)
FIG. 1B is an enlarged view of section I(B) of the lumen facing surface of the tubular scaffolding of the stent in FIG. 1A.

FIG. 2A is a lumen facing surface view of a section of an example tubular scaffolding for an implantable stent in accordance with the disclosure. Specifically, the section of the tubular scaffolding depicted includes an individual strut 100 (uniform in width in the L-axis longitudinally through the strut) having respective sides 115, 120 along a discrete section or region thereof on which is arranged an associated structural extension member (e.g., flap or wing) 225, 225', respectively. It is evident by comparing the same section of the example tubular scaffolding in FIG. 2A with that of the conventional tubular scaffolding in FIG. 1A, that each structural extension member 225, 225' increases the overall/cumulative surface area and larger width (in the y-direction) beyond the respective sides 115, 120 of the individual strut 100. The structural extension members 225, 225' in the example of FIG. 2A are arranged fully aligned along the respective sides 115, 120 of the individual strut 100, wherein the "sides" of the strut represent the surfaces extending from the lumen facing surface 110 to the opposing tissue facing surface 105. In other words, the structural extension members 225, 225' extend outward in the y-direction (perpendicular to the longitudinal L-axis through the individual strut in the x-direction) from respective sides 115, 120 of the individual strut 100. The structural extension members 225, 225' thus alter the radial cross-sectional shape of that section of the tubular scaffolding such that it is no longer uniform in width in the direction of the L-axis between adjacent common vertex thereby providing a larger cumulative overall surface area.

By way of example, in FIGS. 2A-2E the structural extension members are a pair of flaps or wings 225, 225' extending outward in the y-direction (perpendicular to the L-axis longitudinally through the individual strut (i.e., x-direction)) from respective sides 115, 120 of the individual strut 100. FIG. 2B is an end view of the section of example tubular scaffolding 200 in FIG. 2A showing the altered lateral cross-sectional shape as a result of the flap or wing 225, 225' extending outward in the y-direction from the respective sides 115, 120 of the individual strut 100. Flaps or wings 225, 225' may be either integral as a single unit with or a separate component fixedly attached, secured or mounted (e.g., via welding or biocompatible adhesive) to a respective side 115, 120 of the associated individual strut 100. In the case of two separate components, attachment to the individual strut occurs while the flaps or wings 225, 225' are fully extended outward, i.e., no portion of the flaps or wings are twisted, wrapped, or wound about the individual strut 100.

Figure 1C:
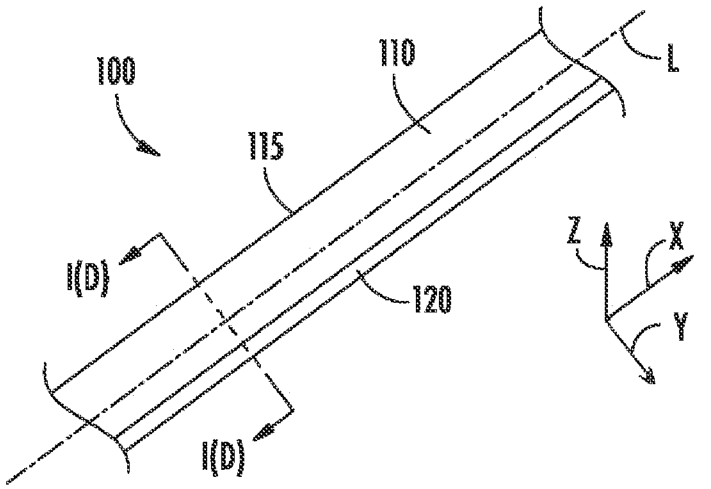
FIG. 1C (PRIOR ART)
FIG. 1C is an enlarged view of the lumen facing surface view of a section I(C) of an individual strut of the tubular scaffolding in FIG. 1B.
Figure 1D:
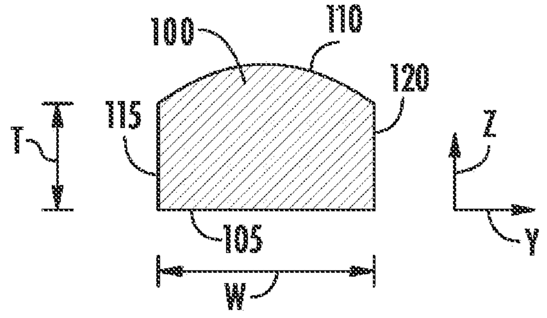
FIG. 1D (PRIOR ART)
FIG. 1D is a radial cross-sectional view through the individual strut in FIG. 1C along lines I(D)-I(D)

In the example in FIG. 2A, flaps or wings 225, 225' extending outward in a y-direction beyond the respective sides 115, 120 of the individual strut 100 are identical (i.e., mirror images of one another on respective left and right sides of the longitudinal L-axis through the strut), and thus only one of the flaps or wings 225, 225' will be described in detail. Viewing the lumen facing surface 210 of the individual strut 100 in FIG. 2A, the center vertical rectangle depicts the conventional individual strut 100 (FIG. 1C) of uniform width to which the present inventive flaps or wings 225, 225' extend outward (in the y-direction) beyond respective sides 115, 120 thereof and are integral with or fixedly attached thereto. The flaps or wings 225, 225' alter the radial cross-sectional shape (i.e., increase in width) of the tubular scaffolding thereby providing a larger overall or cumulative surface area. Irrespective of the state of the implantable stent (e.g., deployed/non-deployed; radially compressed/radially expanded) the flaps or wings 225, 225' remain integral with or fixedly secured to the one or more sides 115, 120, respectively, of the individual strut 100. In addition, the flaps or wings 225, 225' extend fully outstretched in the y-direction (perpendicular to the x-direction parallel with the L-axis) regardless of the state (e.g., non-deployed/deployed; radially compressed/radially expanded) of the implantable stent.

Each flap or wing 225, 225' extends outward in the y-direction from respective sides 115, 120 of the individual strut 100 forming bulging/enlarged discrete sections having an increased/greater surface area relative to those remaining regions in which no flap or wing is present. Furthermore, when viewed from either the lumen facing surface 210 or the opposite tissue facing surface 205 each flap or wing 225, 225' in the example of FIG. 2A has a curved (i.e., convex) border, perimeter or free edge 240, 240' in the x-y-plane resembling that of the side profile of an inflated balloon. A non-curved shape border, perimeter or free edge in the x-y plane of each flap or wing is possible, for instance, rectangular, square or trapezoidal shape. Moreover, the border, perimeter or free edge 240, 240' of all of the flaps or wings 225, 225' in FIGS. 2A-2E are, but need not necessarily be, identical.

For example, the border, perimeter or free edge 240 of flap or wing 225 may be curved (e.g., convex), while the border, perimeter or free edge 240' of flap or wing 225' may be trapezoidal. Dissimilarly shaped flaps or wings on adjacent struts may be selected so as to be efficiently nestable/packable together minimizing the volume occupied when the tubular scaffolding is in the crimped/compressed state (i.e., non-deployed state) within the lumen of the delivery catheter during delivery through the vasculature to the target site.

In the example in FIGS. 2A-2E, flaps or wings 225, 225' on opposing sides 115, 120, respectively, of the individual strut 100 are fully aligned with one another in the direction of the longitudinal L-axis. Alternatively, successive flaps or wings 225, 225' associated with opposing sides 115, 120, respectively, of the individual strut 100 may be staggered or offset (e.g., fully offset (i.e., no overlap)(as depicted in FIG. 2E) or partially offset (i.e., some, but not complete, overlap) from one another in the x-direction of the longitudinal L-axis. Still further, flaps or wings 225, 225' in FIGS. 2A-2C are identical in both profile and dimension but may otherwise be selected to have different profiles and/or associated dimensions. Some, but not necessarily every one, of the individual struts 100 comprising the present inventive implantable stent may have an associated flap(s) or wing(s) on one or both sides 115, 120 thereof.

The thickness "T" in the z-direction (i.e., the distance between the lumen facing surface 210 and the opposite tissue facing surface 205) of each flap or wing 225, 225' is preferably tapered, diminished or reduced (FIGS. 2B & 2C) in the y-direction extending outward from the interface or boundary of the respective sides 115, 120 of the associated individual strut 100. Flaps or wings 225, 225' in the section of example tubular scaffolding in FIG. 2B are identical in shape and dimension. Along the interface or boundary with the respective side of the associated individual strut 100 each flap or wing 225, 225' has a maximum thickness "Tmax" tapering (i.e., reducing) extending outward therefrom in the y-direction with a minimum thickness "Tmin" at the curved border, perimeter or free edge 240, 240'. The maximum thickness "Tmax" of each flap or wing 225, 225' is substantially equal, preferably equal, to the thickness at the boundary or interface of the associated individual strut 100. Along the boundary of the individual strut 100 and associated flap or wing 225, 225', any de minimis difference in thickness is minimized to optimize a continuous, smooth transition therebetween.

In FIGS. 2A-2E, to ensure a continuous, smooth transition at the interface or boundary therebetween, the lumen facing surface 210 and tissue facing surface 205 of the associated flap or wing 225, 225' preferably follows unchanged the contour or profile of the respective lumen facing surface 110 and the tissue facing surface 105 of the associated individual strut 100, as shown in FIG. 2B. Thus, at the boundary or interface, the maximum thickness "Tmax" (in the z-direction) of each flap or wing 225, 225' is preferably equal to the thickness at that point of the respective side 115, 120 of the associated individual strut 100 to which it extends outward from in the y-direction. This is clearly visible in the end view of the tubular scaffolding 200, as represented in FIG. 2B, in which the thickness is approximately equal at the interface, boundary or transition of the flap or wing 225, 225' and the respective sides 115, 120 of the associated individual strut 100. Furthermore, in the exemplary configuration in FIGS. 2A-2E, the lumen facing surface 210 of the flaps or wings 225, 225' has a curved contour or profile continuing or following unchanged the curved contour or profile of the lumen facing surface 110 of the associated individual strut 100. Designing the lumen facing surface 110 of the individual strut 100 with a curved contour or profile advantageously minimizes any turbulent effect on blood flow through stent. Similarly, the tissue facing surface 205 of the flaps or wings 225, 225' in FIG. 2B are planar or flat continuing or following (i.e., unaltered or unchanged from) the planar or flat tissue facing surface 105 of the individual strut 100. This results in a smooth or continuous interface between the flaps or wings 225, 225' and individual strut 100 along both the lumen facing surface and the tissue facing surface that minimizes potential friction and prevents traumatic injury to the surrounding bodily tissue.

Tapering the thickness (in the z-direction) of the flaps or wings 225, 225' provides several benefits: (i) the maximum thickness "Tmax" of the flap or wing at the interface with the respective sides 115, 120 of the individual strut 100 provides strain relief and enhanced strength of attachment between the components (when two separate components); and (ii) the minimum thickness "Tmin" along the border, perimeter or free edge 240, 240' of the flap or wing 225, 225' encourages growth of the surrounding tissue in the growth promoting structural elements (e.g., through holes) closest thereto, as described in further detail below.

Each flap or wing 225, 225' has a plurality of growth promoting structural elements (e.g., through holes, recesses and/or raised elements relative to the tissue facing surface 205) that serve as targeted microsites fostering growth of the surrounding tissue thereto when the stent is implanted in the vessel. The growth promoting elements may include: (i) blind openings (e.g., recesses, wells, grooves or indentations) defined in the tissue facing surface 205 of the flap or wing 225, 225' without extending through to the lumen facing surface 210; (ii) through openings (e.g., holes or perforations) extending from the tissue facing surface 205 through to the lumen facing surface 210 of the flap or wing 225, 225'; and/or (iii) raised elements (e.g., projections, bumps, ribs or other surfaces that may be regular or irregular in shape) relative to the tissue facing surface 205 of the flap or wing 225, 225'. In the case of raised elements, the exposed surface thereof is preferably textured, uneven, rough or non-smooth to foster growth of the surrounding tissue thereto. Any combination of growth promoting structural elements (e.g., through holes, blind holes/recesses and/or raised elements) may be associated in any desired combination or arrangement with any structural extension member. Furthermore, parameters (e.g., type (such as through hole, blind hole and/or raised element), number, arrangement, shape and/or size (dimension)) of the growth promoting structural elements associated with each of the structural extension members may be the same or different.

Accordingly, the number, arrangement, shape and/or size (dimensions) of the structural extension members on an associated individual strut as well as the type number, arrangement, shape and/or size of the growth promoting structural elements for each structural extension member may be selected, as desired.

By way of illustration only, in the section of the example tubular scaffolding 200 depicted in FIGS. 2A-2E the growth promoting structural elements (e.g., through holes) are identical in each flap or wing 225, 225'. That is, the seven through holes (235*a*, 235*b*, 235*c*, 235*d*, 235*e*, 235*f*, 235*g*) defined in flap or wing 225 are identical in shape, size and arrangement to the seven through holes (235'*a*, 235'*b*, 235'*c*, 235'*d* 235'*e*, 235'*f*, 235'*g*) defined in flap or wing 225'.

Each through hole (235*a*, 235*b*, 235*c*, 235*d*, 235*e*, 235*f*, 235*g*, 235'*a*, 235'*b*, 235'*c*, 235'*d* 235'*e*, 235'*f*, 235'*g*) extends (in the z-direction) through the respective flap or wing 225, 225' from its lumen facing surface 210 to its tissue facing surface 205. The through holes (235*a*, 235*b*, 235*c*, 235*d*, 235*e*, 235*f*, 235*g*, 235'*a*, 235'*b*, 235'*c*, 235'*d* 235'*e*, 235'*f*, 235'*g*) in the section of example tubular scaffolding in FIG. 2A are hexagon shape. Any geometric shape opening (e.g., regular or irregular shape) may be used such as a circle, a triangle, a square, a rectangle, a pentagon, etc. For any single flap or wing 225, 225' all the through holes therein need not be the same shape. In addition, the size (i.e., dimension) of each of the through holed associated with any single flap or wing 225, 225' may be, but preferably are not, identical or equal. Most preferably, those through holes (235*a*, 235'*a*) arranged closest to the interface or boundary with the respective sides 115, 120 of the individual strut 100 are largest in size (i.e., dimension) while those through holes (235*g*, 235'*g*) arranged closest to the border, perimeter or free edge 240 240' of the flap or wing 225, 225' are smallest in size (i.e., dimension).

The growth promoting structural elements associated with each structural extension member (e.g., flap or wing 235) may be arranged as a series of arrays (e.g., linear and/or non-linear). Arrangement as a series of arrays allows maximum packing or optimized density per unit area of the growth promoting structural elements.

Referring once again to the section of example tubular scaffolding in FIG. 2A, the through holes are arranged as a plurality of linear arrays extending in an x-direction (parallel to the L-axis longitudinally through the strut 100) and an outermost array (furthest in the y-direction from the respective sides 115, 120 of the individual strut 100) follows the respective border, perimeter or free edge 240. 240' of the associated flap or wing 225, 225'. The non-linear outermost array of growth promoting structural elements 235*g*, 235'*g* in FIG. 2A follows the curved (bulging) border, perimeter or free edge 240 240' of the associated flap or wing 225, 225'. Each flap or wing 225, 225' has associated therewith six linear arrays of holes or openings (235*a*, 235*b* 235*c*, 235*d*, 235*e*, 235*f*) (235'*a*, 235'*b*, 235'*c*, 235'*d*, 235'*e*, 235'*f*), respectively, but any number of linear arrays or even no linear arrays at all are possible.

Moreover, in FIGS. 2A-2E each of the through holes in any given linear array are equal in size (i.e., dimension), however, it is possible for the through holes in any given linear array not to be identical in size (i.e., dimension). When advancing in the y-direction outward from the respective sides 115, 120 of the individual strut 100, the through holes within a particular wing or flap 225, 225' may progressively decrease in size (i.e., dimension). For instance, progressing in the y-direction outward from the respective sides 112, 120 of the individual strut 100, the through the holes or openings in each successive linear array may be smaller in size (i.e., dimension) relative to that of the preceding linear array closer to the sides 115, 120 of the strut 100. Even if not progressively smaller in size (i.e., dimension), nevertheless, the through holes or openings in the innermost array 235*a* (closest in the y-direction to the respective sides 115, 120 of the strut 100) preferably have the largest size (i.e., dimension), while those in the outermost or border array 235*g* (i.e., furthest in the y-direction from the respective sides 115, 120 of the individual strut 100) have the smallest size (i.e., dimension). In addition, the outermost or border array of through holes 235*g*, 235*g'* preferably follows the contour or profile of the border, perimeter or free edge 240, 240' of the respective flap or wing 225, 225' to promote ingrowth of the surrounding tissue therein along the entire border, perimeter or free edge, but this outermost array may be omitted altogether. In the example in FIGS. 2A-2E, the last array 235*g*, 235'*g* is non-linear, following the non-linear curved border, perimeter or free edge 240, 240' of each flap or wing 225, 225' of the individual strut 100. The through holes in any given one of the arrays (albeit linear or non-linear) may but need not necessarily, all be equal. Furthermore, in FIGS. 2A-2E, the outermost or border array of through holes 235*g*, 235*g'* extends along the entire border, perimeter or free edge 240, 240' of the respective flap or wing 225, 225'. Alternatively, the outermost or border array may extend along only one or more discrete portions of the border, perimeter or free edge 240, 240' of the respective flap or wing 225, 225' with portions of the border, perimeter or the free edge 240, 240' being devoid of such holes or openings. Everything described above regarding modifying, as desired, the size (i.e., dimension) and/or arrangement of the through holes is also applicable to blind holes (e.g., recesses) and/or raised elements as the growth promoting structural element.

Different processing techniques may be employed to manufacture the example tubular scaffolding of individual struts in a desired pattern wherein at least some of the individual struts have an associated structural extension member with a plurality of growth promoting structural elements. The tubular scaffolding comprising a plurality of struts arranged in a desired predetermined pattern may be an integral single unit manufactured from a single piece of material having a tubular structure. Spaces are defined by removing (e.g., via laser cutting, mechanical cutting, stamping, perforating or punching) sections or portions of a hypotube made of a single piece of material (e.g., biocompatible material such as Nitinol), while those remaining areas of the hypotube represent the individual struts and associated structural extension members (e.g., flaps or wings) integral thereto as a single unit. It is also contemplated that the individual struts and associated structural extension members (e.g., flaps or wings) integral thereto as a single unit may be manufactured by additive processing (e.g., 3D printing), rather than via removal processing of a preformed tubular structure (e.g., hypotube). Alternatively, the tubular scaffolding may be produced by weaving or braiding individual wires. One or more structural extension members (e.g., wings or flaps) are then secured, mounted or attached (e.g., via adhesive or laser welded) to individual struts along respective sides (i.e., surfaces extending between the lumen facing surface and the opposing tissue facing surface).

Regardless of the method of manufacture, the lumen facing surface of the individual struts of the formed tubular scaffolding, as described in the preceding paragraph, may be subject to post-processing techniques (e.g., laser etching, laser carving and/or further laser cutting) to achieve a desired shape contour or profile. For instance, the lumen facing surface of the individual struts of the formed tubular scaffolding having a square or rectangular lateral cross-sectional shape may be subject to additional post-processing (e.g., laser etching, laser carving and/or laser cutting) to achieve the desired final curved, domed, humped or convex lumen facing surface 110, as depicted in the example shown in FIG. 2D. Post processing may be performed on the lumen facing surface of the individual struts of the formed tubular scaffolding to achieve any desired shape contour or profile. Post-processing (e.g., laser etching, laser carving and/or laser cutting) may also be performed on the lumen facing surface 210 of the structural extension members 225, 225' (e.g., flaps or wings) to achieve a desired tapered contour or profile (e.g., linear or curved) from Tmax to Tmin, such as the tapered curve contour or profile represented in FIG. 2B.

During fabrication, the growth promoting structural elements (e.g., through holes; blind holes/recesses and/or raised elements) associated with an associated structural extension member may be created at various stages during the fabrication process. The growth promoting structural element may be created during initial processing (e.g., laser cutting) when the individual struts and associated structural extension members are manufactured as an integral single unit from a single piece of material (e.g., hypotube) or post-processing thereafter (i.e., laser etching, laser carving or further laser cutting). Similarly, creating the growth promoting structural elements in the structural extension members may occur prior to, during or after being secured, attached or mounted to the associated individual struts, when manufactured as two separate (i.e., non-integral) components. Through holes representing the growth promoting structural elements may be defined in the structural extension members using conventional removal techniques such as perforating, punching or laser cutting. Whereas, recess (i.e., blind hole) growth promoting structural elements are typically created in the tissue facing surface of the structural extension member via laser etching. Lastly, raised elements as the growth promoting structural elements may be created: (i) at the time of manufacture (e.g., during initial molding) of the structural extension member prior to being attached to the individual strut (in the case of separate components); or (ii) during post-processing (e.g., 3D printing) in the case of a single integral unit. At the time of manufacture (e.g., during initial removal processing (e.g., laser cutting) to form the tubular scaffolding or thereafter (e.g., during post-processing via additive or removal processing), the timing and processing technique used to create the growth promoting structural features in the associated structural extension member may be selected, as desired.

FIGS. 2A-2E depict the example tubular scaffolding including a plurality of individual struts 225, 225' with a curved, domed, humped, convex (non-planar) lumen facing surface 110 and an opposite planar (flat) tissue facing surface 105. In another example the individual struts of the tubular scaffolding both the lumen facing surface and opposite tissue facing surface of the individual struts may be planar (i.e., flat) and parallel to one another. Along the boundary, interface or transition between the planar (i.e., flat) lumen facing surface of the individual strut and the structural extension member (e.g., flap or wing) associated therewith, any deviation (i.e., stepwise transition) in thickness is de minimis to optimize a smooth and continuous boundary, interface or transition therebetween. The tapered contour or profile of the lumen facing surface of the structural extension member in the y-direction outward from the associated individual strut may be curved (e.g., similar to that of the lumen facing surface 210 in FIG. 2B) or linear/flat/planar.

Regardless of the manufacturing process used, the final formed implantable stent is delivered through the vasculature to the target site using conventional techniques (e.g., microcatheters, guide wires, etc.). By way of illustrative example, a guidewire may traverse through the vasculature to the distal side of the aneurysm in the brain. Thereafter, a microcatheter is tracked over the guidewire to the target site followed by withdraw of the guidewire from the body. While in a radially compressed (i.e., non-deployed) state the implantable stent is advanced through the lumen of the microcatheter. As the microcatheter is withdrawn in the proximal direction, the implantable stent when unsheathed from the microcatheter deploys across the aneurysm and self-expands radially. During delivery and thereafter upon deployment of the implantable stent, irrespective of its state (e.g., non-deployed/radially compressed vs. deployed/radially expanded) each structural extension member remains fixedly secured to, fully extended outward in the y-direction from, and unaltered in its arrangement relative to the associated individual strut. With the passage of time, the cells of the surrounding tissue grow into and/or atop the growth promoting structural elements (e.g., through holes, blind holes/recesses and/or raised elements) thereby retaining the implantable stent stationary or unchanging (i.e., de minimis, if any movement) in position at the target site within the vessel. Stability is thus provided to the present inventive implantable stent eliminating the need for any separate, distinct, independent mechanical securing component (e.g., sewn anchoring sutures, mechanical fasteners or mechanical clips). Once deployed in the vessel at the target site, with the passage of time, the implantable stent is retained in position by promoting growth of the surrounding tissue thereto without the need for subsequent affirmative securing steps, actions or physical manipulation on the part of the interventionalist.

Moreover, since growth of the cells of the surrounding tissue in and/or atop the growth promoting structural elements occurs over the passage of time in accordance with the example disclosure, the extent or strength to which the implantable stent is stationarily retained in position within the vessel increases with the passage time. In contrast to the use of conventional anchoring sutures or other mechanical securing components wherein the strength to which the implantable stent is retained in position in the vasculature does not increase with the passage of time.

Example 1

An implantable stent comprising: a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen;

wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces radially inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements.

Example 2

The implantable stent of Example 1, wherein the at least one structural extension member is integral with as a single unit or attached as a separate component to the associated one of the individual struts.

Example 3

The implantable stent of any of Examples 1 through 2, wherein the at least one structural extension member is disposed on each of the opposing sides of the associated individual strut; and wherein the at least one structural extension member disposed on each of the opposing sides of the associated individual strut are fully aligned, partially overlapping or fully offset in a direction of the longitudinal axis from one another.

Example 4

The implantable stent of any of Examples 1 through 3, wherein the at least one structural extension member has a free edge; and the at least one structural extension member is tapered in thickness in a direction perpendicular to the longitudinal axis of the associated individual strut such that a maximum thickness is along an interface at one of the opposing sides of the associated individual strut and a minimum thickness along the free edge.

Example 5

The implantable stent of any of Examples 1 through 4, wherein the lumen facing surface of each of the plurality of individual struts has a curved profile and the lumen facing surface of the at least one structural extension member follows the curved profile of the lumen facing surface of the associated individual strut.

Example 6

The implantable stent of any of Examples 1 through 4, wherein both the lumen facing surface and the tissue facing surface of each of the plurality of individual struts are planar.

Example 7

The implantable stent of any of Examples 1 through 6, wherein the plurality of growth promoting structural elements of the associated structural extension member are: (i) through holes; (ii) blind holes defined in the tissue facing surface of the associated structural extension member; and/or (iii) at least one raised element on the tissue facing surface of the associated structural extension member.

Example 8

The implantable stent of any of Examples 1 through 7, wherein the plurality of growth promoting structural elements are arranged with those growth promoting structural elements disposed closest to the interface with the associated individual strut being largest in size while those disposed closest to the free edge of the structural extension member being smallest in size.

Example 9

The implantable stent of any of Examples 1 through 8, wherein the plurality of growth promoting structural elements are arranged so that their size progressively decreases in the direction perpendicular to the longitudinal axis of the associated individual strut.

Example 10

The implantable stent of any of Examples 1 through 9, wherein at least some of the plurality of growth promoting structural elements of the associated at least one structural extension member are arranged in a series of linear arrays.

Example 11

The implantable stent of any of Examples 1 through 10, wherein the tubular scaffolding is transitionable between a radially compressed state and a radially expanded state; and irrespective of the state of the tubular scaffolding, positioning of the at least one structural extension member relative to the associated individual strut remains unchanged.

Example 12

A method of manufacturing an implantable stent including a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen; wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces radially inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements; the method comprising the steps of: providing the tubular scaffolding comprising the plurality of individual struts arranged in the pattern and the at least one structural extension member associated with one of the individual struts; and creating the plurality of growth promoting structural elements in the at least one structural extension member.

Example 13

The method of Example 12, wherein the plurality of individual struts and the at least one structural extension member are integral as a single unit or two separate components attached to one another.

Example 14

The method of any of Examples 11 through 13, wherein the providing step comprises removing sections of a hypotube made of a single piece of material to simultaneously produce the plurality of individual struts and the at least one structural extension member associated with one of the individual struts integral as a single unit; and wherein the creating step is performed during or after the removal step.

Example 15

The method of Example 14, during or after the removing step, further comprising the step of stripping away a portion of the lumen facing surface of the at least one structural extension member to produce a tapered profile.

Example 16

The method of Example 14, during or after the removing step, further comprising the step of taking off: (i) a portion of the lumen facing surface of the at least one structural extension member to produce a tapered profile; and (ii) a portion of the lumen facing surface of each of the plurality individual struts to produce a non-planar profile.

Example 17

The method of any of Examples 12 through 16, wherein the providing step comprises the steps of: weaving or braiding multiple wires together to produce the tubular scaffolding comprising the plurality of individual struts; and attaching the at least one structural extension member to one of the opposing sides of the associated individual strut.

Example 18

The method of Example 17, wherein the creating step is performed prior to, during or after the attaching step.

Example 19

A method of using an implantable stent including a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen; wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements; the method comprising the steps of:

delivery and deployment of the implantable stent to a target site in a vessel; and increasing over time, retainment strength of the implantable stent in position at the target site in the vessel due exclusively to growth of tissue cells in and/or atop the growth promoting structural elements.

Example 20

The method of Example 19, wherein the implantable stent is retained at the target site exclusively via growth of tissue cells in and/or atop the growth promoting structural elements without use of mechanical anchors or sutures.

Thus, while there have been shown, described, and pointed out fundamental novel features of the system/device as applied to a preferred example thereof, it will be understood that various omissions, substitutions, and changes in the form and details of the systems/devices illustrated, and in their operation, may be made by those skilled in the art without departing from the spirit and scope of the disclosure. For example, it is expressly intended that all combinations of those elements and/or steps that perform substantially the same function, in substantially the same way, to achieve the same results be within the scope of the disclosure. Substitutions of elements from one described example to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. An implantable stent comprising:

a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen; wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces radially inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements, wherein the at least one structural extension member has a free edge; and the at least one structural extension member is tapered in thickness in a direction perpendicular to the longitudinal axis of the associated individual strut such that a maximum thickness is along an interface at one of the opposing sides of the associated individual strut and a minimum thickness along the free edge.

2. The implantable stent according to claim 1, wherein the at least one structural extension member is integral with as a single unit or attached as a separate component to the associated one of the individual struts.

3. The implantable stent according to claim 1, wherein the at least one structural extension member is disposed on each of the opposing sides of the associated individual strut; and wherein the at least one structural extension member disposed on each of the opposing sides of the associated individual strut are fully aligned, partially overlapping or fully offset in a direction of the longitudinal axis from one another.

4. The implantable stent according to claim 1, wherein the lumen facing surface of each of the plurality of individual struts has a curved profile and the lumen facing surface of the at least one structural extension member follows the curved profile of the lumen facing surface of the associated individual strut.

5. The implantable stent according to claim 1, wherein both the lumen facing surface and the tissue facing surface of each of the plurality of individual struts are planar.

6. The implantable stent according to claim 1, wherein the plurality of growth promoting structural elements of the associated structural extension member are: (i) through holes; (ii) blind holes defined in the tissue facing surface of the associated structural extension member; and/or (iii) at least one raised element on the tissue facing surface of the associated structural extension member.

7. The implantable stent according to claim 6, wherein the plurality of growth promoting structural elements are arranged with growth promoting structural elements disposed closest to the interface with the associated individual strut being largest in size while growth promoting structural elements disposed closest to the free edge of the structural extension member being smallest in size.

8. The implantable stent according to claim 7, wherein the plurality of growth promoting structural elements are arranged so that their size progressively decreases in the direction perpendicular to the longitudinal axis of the associated individual strut.

9. The implantable stent according to claim 7, wherein at least some of the plurality of growth promoting structural elements of the associated at least one structural extension member are arranged in a series of linear arrays.

10. The implantable stent according to claim 1, wherein the tubular scaffolding is transitionable between a radially compressed state and a radially expanded state; and irrespective of the state of the tubular scaffolding, positioning of the at least one structural extension member relative to the associated individual strut remains unchanged.

11. A method of manufacturing an implantable stent including a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen; wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces radially inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements; the method comprising the steps of:

providing the tubular scaffolding comprising the plurality of individual struts arranged in the pattern and the at least one structural extension member associated with one of the individual struts; and creating the plurality of growth promoting structural elements in the at least one structural extension member, wherein the at least one structural extension member has a free edge; and the at least one structural extension member has a tapered profile that is tapered in thickness in a direction perpendicular to the longitudinal axis of the associated individual strut such that a maximum thickness is along an interface at one of the opposing sides of the associated individual strut and a minimum thickness along the free edge.

12. The method according to claim 11, wherein the plurality of individual struts and the at least one structural extension member are integral as a single unit or two separate components attached to one another.

13. The method according to claim 11, wherein the providing step comprises removing sections of a hypotube made of a single piece of material to simultaneously produce the plurality of individual struts and the at least one structural extension member associated with one of the individual struts integral as a single unit; and wherein the creating step is performed during or after the removal step.

14. The method according to claim 13, during or after the removing step, further comprising the step of stripping away a portion of the lumen facing surface of the at least one structural extension member to produce the tapered profile.

15. The method according to claim 13, during or after the removing step, further comprising the step of taking off: (i) a portion of the lumen facing surface of the at least one structural extension member to produce the tapered profile; and (ii) a portion of the lumen facing surface of each of the plurality individual struts to produce a non-planar profile.

16. The method according to claim 11, wherein the providing step comprises the steps of:

weaving or braiding multiple wires together to produce the tubular scaffolding comprising the plurality of individual struts; and attaching the at least one structural extension member to one of the opposing sides of the associated individual strut.

17. The method according to claim 16, wherein the creating step is performed prior to, during or after the attaching step.

18. A method of using an implantable stent including a tubular scaffolding having a proximal end, an opposite distal end and a lumen extending therethrough; the tubular scaffolding including a plurality of individual struts arranged in a pattern defining open spaces therebetween; wherein the tubular scaffolding has a lumen facing surface that faces radially inward toward the lumen and an opposite tissue facing surface that faces radially outward away from the lumen; wherein each of the individual struts has a longitudinal axis and a lateral cross-section with opposing sides extending between the lumen facing surface and the tissue facing surface; and at least one structural extension member associated with one of the individual struts, wherein the at least one structural extension member has a lumen facing surface that faces inward toward the lumen and an opposite tissue facing surface that faces radially outward away from the lumen; the at least one structural extension member extending in a direction perpendicular to the longitudinal axis outward from one of the opposing sides of the associated individual strut; wherein the at least one structural extension member has a plurality of growth promoting structural elements; the method comprising the steps of:

delivery and deployment of the implantable stent to a target site in a vessel; and increasing over time, retainment strength of the implantable stent in position at the target site in the vessel due exclusively to growth of tissue cells in and/or atop the growth promoting structural elements, wherein the at least one structural extension member has a free edge; and the at least one structural extension member has a tapered profile that is tapered in thickness in a direction perpendicular to the longitudinal axis of the associated individual strut such that a maximum thickness is along an interface at one of the opposing sides of the associated individual strut and a minimum thickness along the free edge.

19. The method according to claim 18, wherein the implantable stent is retained at the target site exclusively via growth of tissue cells in and/or atop the growth promoting structural elements without use of mechanical anchors or sutures.

* * * * *